United States Patent [19]

Bock et al.

[11] 4,124,569

[45] Nov. 7, 1978

[54] PROCESS FOR THE PREPARATION OF POLYISOCYANATES CONTAINING URETHANE AND BIURET GROUPS

[75] Inventors: Manfred Bock, Leverkusen; Josef Pedain, Cologne; Walter Uerdingen, Bergisch-Gladbach; Manfred Schönfelder, Leverkusen, all of Germany

[73] Assignee: Bayer Aktiengesellschaft, Leverkusen Bayerwerk, Germany

[21] Appl. No.: 832,318

[22] Filed: Sep. 12, 1977

[30] Foreign Application Priority Data

Sep. 15, 1976 [DE] Fed. Rep. of Germany ....... 2641448

[51] Int. Cl.$^2$ ............................................. C08G 18/79
[52] U.S. Cl. ........................................ 528/61; 528/65; 528/59
[58] Field of Search ...... 260/775 AT, 75 NT, 75 NQ, 260/77.5 AQ

[56] References Cited

U.S. PATENT DOCUMENTS

| | | | |
|---|---|---|---|
| 3,647,848 | 3/1972 | Wagner et al. ................. | 260/75 NT |
| 3,824,266 | 7/1974 | Dietrich et al. ............. | 260/77.5 AT |
| 3,862,973 | 1/1975 | Dietrich et al. ............. | 260/77.5 AT |
| 3,903,126 | 9/1975 | Woerner et al. ............. | 260/77.5 AT |
| 3,903,127 | 9/1975 | Wagner et al. ............. | 260/77.5 AT |
| 3,943,158 | 3/1976 | Dietrich et al. ............. | 260/77.5 AT |
| 3,976,622 | 8/1976 | Wagner et al. ............. | 260/77.5 AT |

*Primary Examiner*—H.S. Cockeram
*Attorney, Agent, or Firm*—Gene Harsh; Lawrence S. Pope

[57] ABSTRACT

The present invention is concerned with a process for producing biuret polyisocyanates and the polyisocyanates so produced. These isocyanates are produced by the reaction of at least about a four fold molar excess of a diisocyanate having aliphatically bound isocyanate groups with amino alcohols having a particular structure at a temperature between about 90 and 200° C. The amino alcohols contain at least three carbon atoms, have their hydroxyl and amino groups separated by at least two carbon atoms, and may contain urea, urethane, ether or amino bonds. The present invention is also concerned with a process for producing two component and one component moisture curing lacquers using the biuret polyisocyanates of the present invention and the lacquers so produced.

16 Claims, No Drawings

PROCESS FOR THE PREPARATION OF POLYISOCYANATES CONTAINING URETHANE AND BIURET GROUPS

FIELD OF THE INVENTION

This invention relates to a process for the preparation of new polyisocyanates containing biuret and urethane groups and to their use.

BACKGROUND OF THE INVENTION

Aliphatic polyisocyanates which contain biuret groups have become of considerable commercial importance in the field of films and coatings. They are prepared from aliphatic diisocyanates and water, compounds from which water can be split off or compounds which are capable of liberating an amino group under certain conditions. Polyisocyanates which contain biuret groups can also be prepared by the direct reaction of amines and polyamines with diisocyanates.

It is also known that the biuret group is comparatively unstable under the conditions of the biuretization reaction so that the monoamine or polyamine used as starting material very readily changes into the corresponding isocyanate by "transbiuretization". Thus, for example, simply by reacting a high boiling diisocyanate with a monoamine it is possible to obtain the monoisocyanate corresponding to the monoamine by distillation. A polyisocyanate which contains biuret groups remains behind as distillation residue.

As is to be expected, this reaction also takes place when a diamine is reacted with excess diisocyanate to form urea and the reaction product is then biuretized. Here again, an equilibrium reaction takes place with the diisocyanate which is usually used in excess, to form the diisocyanate corresponding to the diamine put into the reaction. When the reaction mixture is subsequently purified by distillation to isolate the biuret polyisocyanate, the distillate contains not only the diisocyanate originally put into the process but also a second diisocyanate corresponding to the diamine put into the process. Alternatively, if a high boiling diamine is used, distillation of the diisocyanate originally put into the process results mainly in solutions of the biuret polyisocyanate in the diisocyanate which corresponds to the diamine. Thus, for example, when the method of preparation described in Example 13 of German Offenlegungsschrift 2,261,065 is carried out, the reaction of hexamethylene diisocyanate with 3,3'-dimethyl-4,4'-diamino dicyclohexyl methane results not only in the biuret polyisocyanate specified there but, in addition, more than 10% by weight of 3,3'-dimethyl-4,4'-diisocyanato-dicyclohexyl methane. This can easily be demonstrated, for example, by gas chromatographic analysis. Similar results are obtained when other examples described in German Offenlegungsschrift 2,261,065 are repeated, that is to say a monomeric diisocyanate corresponding to the diamine is formed in addition to the biuret polyisocyanate.

More recent tests have shown that when biuret polyisocyanate mixtures which can easily be produced with a maximum free diisocyanate content (for example, hexamethylene diisocyanate) of 0.7% are subjected to prolonged storage, in particular under uncontrolled conditions, for example, when transported by sea in hot climates, the proportion of monomeric diisocyanate is liable to increase again over a period of a few months and may rise to over 1%. This is due to catalytic reactions with the walls of glass or metal containers and possibly also due to catalytic effects of impurities which cannot be identified analytically, and occurs particularly at elevated temperatures.

When products prepared from a diamine and a diisocyanate (e.g. according to German Offenlegungsschrift 2,261,065, Example 13) have been stored for a long time or at elevated temperatures, e.g. at 50° C., they are found to contain two monomer diisocyanates:

(1) More than 10% by weight of the diisocyanate already mentioned above which corresponds to the diamine used as starting material; and (2) About 1 to 2% by weight of the diisocyanate used as starting material.

Toxicological investigations and many years experience in the processing of biuret polyisocyanates and lacquer binders, have shown that there is no danger in using the lacquers mentioned above under the protective conditions normally employed for lacquer processing if the biuret polyisocyanates used in the process do not contain more than 0.7% of free diisocyanate (e.g. hexamethylene diisocyanate). The limit of 0.7% has been accepted in the memorandum "PUR-Anstrichstoffe" published by the Association of German Industrial and Trade Unions and in the "Polyurethane-Report" of the Paintmakers Association.

Apart from these toxicological considerations, the presence of a low boiling monomeric isocyanate in a polyisocyanate which is intended to be used for lacquers and coatings is a major disadvantage. Monomeric isocyanates are liable to evaporate with the solvent before the lacquer has completely hardened. This is liable to produce defects in the surface of the lacquers and occurs most commonly when rapid drying is carried out at elevated temperatures. On the other hand, it is often necessary to dry a lacquer under such stringent conditions because the reactivity of lacquer polyisocyanates which contain too high a proportion of isocyanates which are not more than difunctional is very low. High quality polyurethane lacquers are generally obtained from polyfunctional polyisocyanates.

A biuret polyisocyanate based on hexamethylene diisocyanate and stabilized against decomposition has been disclosed in German Offenlegungsschrift 2,437,130.

The stability of this polyisocyanate is obtained by the presence of N-formyl groups so that the polyisocyanate mixture contains a substantial proportion of the following compound:

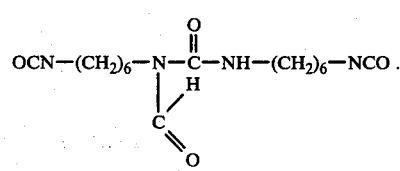

The advantage of the high stability of this biuret polyisocyanate mixture is offset by various disadvantages in its practical application. These are due to the low isocyanate functionality. Since the product contains the difunctional compound shown above, the average functionality is less than 3. Lacquers produced from this product therefore harden only slowly and often have too little initial hardness.

The present invention makes it possible to obtain new biuret polyisocyanates which combine all the advantages of the known polyisocyanates which have have a biuret structure and, in addition, no longer have the disadvantage of decomposing into the original monomeric diisocyanate during prolonged storage. The new polyisocyanates with biuret groups contain urethane groups in addition to these biuret groups and are prepared by the reaction of certain compounds with amino and hydroxyl groups which will be defined in more detail below with excess quantities of simple diisocyanates.

The reaction of amino alcohols with aromatic and aliphatic diisocyanates and derivatives thereof is not new and belongs to the state of the art. Thus, for example, amino alcohols are commonly used chain lengthening agents for the production of polyurethane elastomers. In German Offenlegungsschriften 1,720,747; 2,031,408 and 2,242,520 there also mentioned, among others, addition products of up to 3 mols of aliphatic diisocyanate with amino alcohols, without these products being described in any detail. There is no evidence from these citations that the products mentioned there contain biuret groups or that they constitute polyisocyanates which are resistant to decomposition into the original monomers.

Moreover, it is clear from the comparison experiments described hereinafter that the amino alcohols mentioned in the aforesaid prior publications are not ideally suitable as starting materials for the preparation of biuret polyisocyanates.

SUMMARY OF THE INVENTION

The present invention relates to a process for the preparation of polyisocyanates with aliphatically bound isocyanate groups and an isocyanate functionality greater than 2 which contain urethane groups and biuret groups, characterized in that aliphatic and/or cycloaliphatic diisocyanates used at least in about a 4-times molar excess are reacted at about 90°-200° C. with compounds of the formula

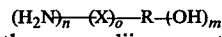

and the excess diisocyanate is subsequently removed. In the above formula,
$o$ represents 0 or 1,
$m$ is 1 or 2 when $o = 0$ and 1 when $o = 1$,
$n$ represents 1 or 2 when $o = 0$ and 1 when $o = 1$ such that the sum of $n + m$ is always 2 or 3,
R represents
(a) a xylylene group when $o = 0$ or
(b) when $o = 0$ it may also represent an aliphatic or cycloaliphatic hydrocarbon group with a total of 3-18 carbon atoms which may be interrupted by secondary amino groups —NH—, ether groups —O—, amido groups —NH—CO— or urethane groups —NH—CO—O— in such a manner that at least two carbon atoms are situated between the NH$_2$— and OH-groups; the trimethylene group is excepted; or
(c) when $o = 1$, R represents an aliphatic hydrocarbon group having from 2 to 10 carbon atoms, at least two carbon atoms being arranged between X and the OH-group;
X represents a group of the formula —NH—CO—O— or —NH—CO—, the amino group —NH$_2$ being in all cases linked to the nitrogen atom of the said group to form the structure of a hydrazine derivative.

The present invention also relates to polyisocyanates with biuret groups and urethane groups which can be obtained by this process.

It also relates to the use of polyisocyanates with biuret and urethane groups obtainable by the process according to the invention as isocyanate components in polyurethane lacquers.

The compounds of the formula

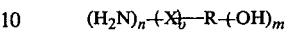

used as biuretizing agent in the process according to the invention may be, for example, any of the following compounds:

1. Amino alcohols of the formula

wherein
$n$ and $m$ have the meaning already mentioned above and preferably both have the value 1, and
R' represents a xylylene group or an aliphatic or cycloaliphatic hydrocarbon group having a total of 3 to 18 carbon atoms with the limitation given above for the definition of R, which hydrocarbon group may be interrupted by amino groups —NH—, ether groups —O—, amido groups —NH—CO— or urethane groups —NH—CO—O. R' preferably represents an aliphatic hydrocarbon group with a total of 4 to 10 carbon atoms which may be interrupted by a urethane group —NH—CO—O— or a cycloaliphatic or mixed cycloaliphatic-aliphatic hydrocarbon group with a total of 6 to 15 carbon atoms which may be interrupted by a urethane group —NH—CO—O.

The following are examples of suitable amino alcohols: 4-amino-1-butanol; 4-amino-2-butanol; 3-amino-1-butanol; 2-amino-1-butanol; 3-amino-3-methyl-1-butanol; 2-amino-2-methyl-propanol-1; 2-amino-2-methyl-propane diol; 2-amino-2-hydroxymethyl-propane diol; 5-amino-1-pentanol; 3-amino-2,2,4-trimethyl-1-pentanol; 6-amino-1-hexanol; methylhexanolamine (isomeric mixture), trimethyl-1,6-hexanolamine (isomeric mixture), 2,2-dimethyl-3-amino-1-hexanol; 7-amino-1-heptanol; 10-amino-1-decanol; 12-amino-1-dodecanol; 2(3 or 4)-amino-cyclohexanol; 2 (or 3)-methyl-4-aminocyclohexanol; 2 (or 6)-methyl-3-amino-cyclohexanol; 5 (or 6)-methyl-2-amino-cyclohexanol; 2 (3 or 4)-aminomethylcyclohexanol; 2(3-aminopropyl)-cyclohexanol; 3-aminomethyl-3,5,5-trimethyl-cyclohexanol; 4-(2-aminoethyl)-(2-hydroxyethyl)-cyclohexane; 1-hydroxymethyl-3(or 4)-aminomethylcyclohexane; 2-hydroxy methyl-5(or 6)-amino methyl-bicyclo-2,2,1-heptane; 1-hydroxy-5(6 or 7)-amino-decahydronaphthalene; 2-hydroxy-6(or 7)-amino-decahydronaphthalene; 1-aminomethyl-2-hydroxy-decahydronaphthalene; 4-amino-4'-hydroxy-dicyclohexylmethane and 2-(4-aminocyclohexyl)-2-(4-hydroxycyclohexyl)-propane.

These amino alcohols are preferably used for the process according to the invention.

Amino alcohols having less than 4 carbon atoms are less suitable for the process of the invention. They give rise to high melting, difficultly soluble ureas which decompose when attempts are made to biuretize them or fork darkcolored reaction products as can be seen from the Comparison Experiments. An exception is the compound 2-amino-propanol-1, which may also be used but is not among the preferred amino alcohols.

Amino alcohols which contain secondary amino groups (> NH) and which may be obtained, for example, by monoaddition of oxiranes with diamines may also be used. The following are examples:

N-(2-aminopropyl)-ethanolamine;
N-(6-aminohexyl)-aminoethanol;
N-(6-aminohexyl)-1(or -2)-methyl-ethanolamine;
N-(3-amino-1,5,5-trimethyl-cyclohexylmethyl)-aminoethanol;
N-(3-amino-1,5,5-trimethyl-cyclohexylmethyl)-1(or -2)-methyl-ethanolamine;
N-(3-amino-1,5,5-trimethyl-cyclohexylmethyl)-1,1 (or -2,2)-dimethyl-ethanolamine and
N-(3-amino-1,5,5-trimethyl-cyclohexylmethyl)-1,2-dimethylethanolamine.

Amino alcohols having an ether structure are also suitable, for example, the following compounds obtained by monoaddition of acrylonitrile to glycols followed by reduction:

HO—(CH$_2$)$_2$—O—(CH$_2$)$_3$—NH$_2$
HO—(CH$_2$)$_4$—O—(CH$_2$)$_3$—NH$_2$
HO—(CH$_2$)$_5$—O—(CH$_2$)$_3$—NH$_2$
HO—(CH$_2$)$_6$—O—(CH$_2$)$_3$—NH$_2$
HO—(CH$_2$)$_2$—O—(CH$_2$)$_2$—O—(CH$_2$)$_3$—NH$_2$

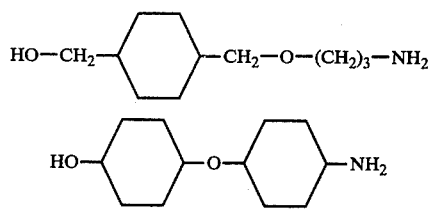

Amino alcohols with amide units (—NH—CO—) which can be obtained, for example, by a ring opening reaction of γ-butyrolactone or γ-caprolactone with diamines may also be used. The following are examples:

N-aminoethyl-3-hydroxypropane carboxylic acid-1-amide;
N-(4-aminobutyl)-5-hydroxypentane carboxylic acid-1-amide;
N-(6-aminohexyl)-5-hydroxypentane carboxylic acid-1-amide and
N-(3-amino-1,5,5-trimethyl-cyclohexylmethyl)-5-hydroxypentane carboxylic acid-1-amide.

Amino alcohols with urethane units, which can be obtained, for example, by reacting cyclic carbonates with diamines, are particularly preferred. The following are examples:

H$_2$N.CH$_2$.CH$_2$.NH.CO.O.CH$_2$.CH$_2$.OH
H$_2$N.CH(CH$_3$).CH$_2$.NH.CO.O.CH$_2$.CH(CH$_3$).OH (isomeric mixture)
H$_2$N.(CH$_2$)$_6$.NH.CO.O.CH$_2$.CH$_2$.OH
H$_2$N.(CH$_2$)$_6$.NH.CO.O.CH$_2$.CH(CH$_3$).OH (isomeric mixture)

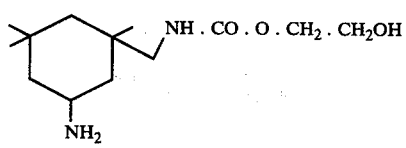

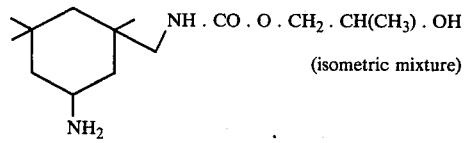
(isometric mixture)

2. Hydrazine derivatives with hydroxyl groups as represented by the formula

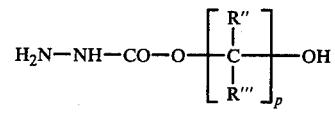

in which
R″ and R‴ represent the same or different groups and represent hydrogen or a C$_1$-C$_4$-alkyl group, preferably hydrogen or a methyl group, and
p preferably represents 2 or 3.

The following are examples:

H$_2$N—NH—CO—O—CH$_2$—CH$_2$—OH
H$_2$N—NH—CO—O—CH$_2$—CH—OH (isomeric mixture)
          |
          CH$_3$ CH$_3$
          |
H$_2$N—NH—CO—O—CH$_2$—C—CH$_2$—OH
          |
          CH$_3$ H$_2$N—NH—CO—O—CH$_2$—CH—CH$_2$—OH or
                  |
                  C$_2$H$_5$ H$_2$N—NH—CO—O—CH$_2$—C—CH$_2$—OH
                 / \
              C$_2$H$_5$  C$_2$H$_5$ These compounds may be prepared by ring opening reactions of cyclic carbonates with hydrazine or hydrazine derivatives.

3. Hydrazine derivatives of the formula

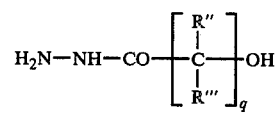

in which
R″ and R‴ have the meaning already indicated, and
q represents an integer of from 4 to 10, preferably 5.

5-Hydroxy-caproic acid hydrazide is a typical example of such compounds. The compounds can easily be prepared by a ring opening reaction of cyclic lactones with hydrazine or hydrazine hydrate.

The biuretizing agents preferably used in the process according to the invention are those amino alcohols which are listed as preferred under 1. Particularly preferred are the amino alcohols with urethane groups mentioned under 1.

Any diisocyanates having aliphatically and/or cycloaliphatically bound isocyanate groups are suitable for the process according to the invention, for example, ethylene diisocyanate; tetramethylene-1,4-diisocyanate; 2,4,4- and 2,4,4-trimethyl-hexamethylene-1,6-diisocyanate; dodecane-1,12-diisocyanate; C$_1$-C$_8$-alkyl esters of lysine diisocyanate; cyclobutane-1,3-diisocyanate; cyclohexane-1,3- and -1,4-diisocyanate and any mixtures of these isomers; hexahydrotolylene-2,4- and 2,6-diisocyanate and any mixtures of these isomers; 3,3'-dimethyl-4,4'-diisocyanato dicyclohexyl methane; 4,4'-diisocyanato-dicyclohexyl methane and xylylene diisocyanate.

The diisocyanates preferably used are hexamethylene diisocyanate and 1-isocyanato-3,3,5-trimethyl-5-isocyanatomethylcyclohexane (isophorone diisocyanate).

The process according to the invention is carried out at temperatures in the range of about 90°-200° C., preferably about 120°-180° C. The quantity of diisocyanate used in the process according to the invention is at least about 4 mole, preferably about 6 to 25 mole, for each mole of biuretizing agent used according to the invention.

The process according to the invention may be carried out, for example, as follows:

6 to 25 mole of an aliphatic or cycloaliphatic diisocyanate are introduced into a stirrer vessel under an inert gas atmosphere (e.g., nitrogen or argon) and heated to 120° to 180° C. 1 mole of the biuretizing agent is then added with vigorous stirring. The reaction mixture is heated to 120°-180° C. for a further period of from 20 minutes to about 3 hours. Any precipitate formed during the first phase of the reaction disappears during this time. The reaction mixture becomes homogeneous. Stirring is continued for a further period of about 15 minutes at 120° to 180° C. and the mixture is then cooled. The excess diisocyanate is removed by a known distillation process (thin layer evaporator) or extraction process (n-hexane). The reaction is preferably carried out at such a temperature that practically no precipitate forms when the biuretizing agent is added to the diisocyanate and the solid reaction products initially formed immediately undergo further reaction. The reaction should, as far as possible, proceed in a homogeneous phase.

The process according to the invention may be carried out with liquid or solid biuretizing agents. Volatile biuretizing agents may be introduced into the diisocyanate in gaseous form, optionally diluted with an inert gas, liquid biuretizing agents are introduced dropwise while solid biuretizing agents are added as such or as melts. A solvents which is inert towards isocyanate groups may also be used, but the process according to the invention is preferably carried out solvent-free. The products of the process are viscous polyisocyanates ranging from colorless to yellow. At room temperature they may be liquid or in the form of solid hard resins. They are completely odorless and form clear solutions in solvents which are inert towards isocyanate groups, such as hydrocarbons, chlorinated hydrocarbons, esters or ketones.

The reactions which take place in the process according to the invention are basically as follows: A urea group and a urethane group are first formed from the $NH_2$ and OH-group. In a second reaction step, a biuret group is formed from the urea group by reaction with diisocyanate.

As a result of these reactions, the main product obtained when using a biuretizing agent which contains an $H_2N$-group and an OH-group is a trifunctional polyisocyanate. However, the polyisocyanates prepared by the process according to the invention also contain by-products, since side reactions cannot be completely excluded at the high temperatures employed for the process. For example, the reaction mixture may contain difunctional components due to the formation of an isocyanate group from the amino group of the amino alcohol by a process of transbiuretization. Moreover, the trifunctional polyisocyanates may also give rise to homologous, higher functional polyisocyanates. Isocyanates prepared by the process according to the invention may also contain a certain proportion of polyisocyanates formed by trimerization of some of the isocyanate groups.

The presence of such by-products which cannot be separated by a simple process is no disadvantage for practical application of the polyisocyanate produced by the process according to the invention. Some of them have an advantageous effect on the viscosity and on the compatibility of the polyisocyanates with their reactants such as polyol compounds. The polyisocyanates prepared by the process according to the invention do not contain any by-products liable to reduce their resistance to decomposition into the original monomeric diisocyanate.

Biuret polyisocyanates prepared from amino alcohols having amide groups (CO—NH) or secondary amino groups (NH) by the process according to the invention contain urea and acylurea groups in addition to urethane groups. The presence of these urea and acylurea groups is due to the reaction of the said amide groups or secondary amino groups with the diisocyanate. Biuret polyisocyanates obtained in this way have an exceptionally high isocyanate functionality, the average value being higher than 3.

Polyisocyanates prepared by the process according to the invention are distinguished from the biuret polyisocyanates known in the art by the following major advantages: They do not split off any free isocyanate, even when stored at 50° C., they can be prepared with a very low viscosity if required and they have an average isocyanate functionality greater than 3.

As a result of these properties, these isocyanates are particularly suitable for the preparation of light-fast two component polyurethane lacquers and moisture hardening one-component polyurethane lacquers and for the production of polyurethane stoving lacquers in the masked form.

The biuret-urethane polyisocyanates used in two-component lacquers, optionally in the blocked form, may be reacted with any compounds having more than one OH, SH, NH, or COOH-group, which may in some cases be formed only in the process of hardening. The following reactants are particularly preferred:

Polyamines, optionally in the form of the corresponding polyketimines, such as ethylene diamine; triethylene tetramine; tetraethylene pentamine; dipropylene triamine; tripropylene tetramine; N-methyl-propylene diamine; hexamethylene diamine; N,N'-bis-cyclohexyl-m-xylylene diamine; N,N'-bis-cyclohexyl-isophorone diamine; the hydrogenated addition products of 2 mol of acrylonitrile to ethylamine; propylamine or ethylene diamine; hydrogenated addition products of $x$ mols of acrylonitrile to polyols; where $x$ is the number of hydroxyl equivalents; hydroxy-containing and/or carboxyl-containing polyethers; polyesters and polymers, e.g., polyethylene oxides, polypropylene oxides, polybutylene oxides and polytetrahydrofurans containing from 2 to 6 hydroxyl groups; corresponding copolymers containing 2 to 6 hydroxyl groups; polyacetyls containing carboxyl and/or hydroxyl groups; polyesters of carbonic, adipic phthalic, tetrahydrophthalic, hexahydrophthalic, endomethylene tetrahydrophthalic and methylhexahydrophthalic acid; polyhydric alcohols, e.g., ethylene glycol, diethylene glycol, triethylene glycol, octaethylene glycol, propylene glycol-(1,2), polypropylene glycol, 2,2-dimethylpropane diol-(1,3), butane diol-(1,3), butane diol-(1,4), 2,2-bis-(4-hydroxycyclohexyl)-propane, 2,2-bis-(4-hydroxyphenyl)-propane, trimethylol propane, glycerol, etc.; hydroxyl-containing and/or carboxyl-containing copolymers of olefinically unsaturated monomers such as styrene, alkyl esters of acrylic acid containing from 1 to 8 carbon atoms in the alkyl group, methacrylic acid alkyl esters containing from 1 to 8 carbon atoms in the alkyl group, acrylonitrile, ethylene, vinyl chloride, vinyl acetate, allyl alcohol, vinyl alcohol, hydroxyethyl and hydroxypropyl esters of acrylic and methacrylic acid, acrylic acid itself, methacrylic acid, maleic acid, fumaric acid, maleic semiesters, etc.

The polyisocyanates prepared by the process according to the invention and their reactants are generally reacted together in proportions such that the reaction mixture contains from about 0.8 to 3, preferably about 0.9 to 1.1 hydroxyl, amino, mercapto and/or carboxyl groups to each, optionally blocked, isocyanate group.

Hardening may be accelerated by means of catalysts commonly used in isocyanate chemistry, e.g., tertiary amines such as triethylamine, pyridine, methyl pyridine, benzyl dimethylamine, N,N-dimethylaminocyclohexane, N-methylpiperidine, pentamethyl diethylene triamine, N,N-endoethylene piperazine, N,N'-dimethyl piperazine, etc.; metal salts such as Iron(III)-chloride, zinc, chloride, zinc-2-ethylcaproate, tin(II)-2-ethylcaproate, dibutyl tin(IV)-dilaurate, molybdenum glycolate, etc.

The above-mentioned reactants with hydroxyl functions are also the ones mainly used with biuret-urethane polyisocyanates in one-component lacquers.

The components are reacted in proportions corresponding to at least about 1.2, preferably about 1.5 to 10 isocyanate groups to one hydroxyl group. The reaction results in lacquer binders which have free isocyanate groups and harden in moist air to form hard, glossy, high quality coatings. The catalysts mentioned above may also be used for one-component lacquers.

When the biuret-urethane polyisocyanates are used in stoving lacquers, the isocyanate groups are partly or completely blocked in known manner. The polyisocyanate is reacted in a suitable blocking agent, preferably at an elevated temperature, e.g., 40°–140° C., optionally in the presence of a suitable catalysts, e.g., tertiary amines, metal salts such as zinc-2-ethyl caproate, tin(II)-2-ethyl caproate, dibutyl tin(IV)-dilaurate or an alkali metal phenolate.

The following are examples of suitable blocking agents: Monophenols such as phenol, cresols, trimethyl phenols, and tertiary butyl phenols; tertiary alcohols such as tertiary butanol, tertiary amyl alcohol and dimethylphenyl carbinol; compounds which readily form enols, e.g., ethyl acetoacetate, acetyl acetone, and malonic acid derivatives such as malonic acid diesters having from 1 to 8 carbon atoms in the alcohol groups; secondary aromatic amines such as N-methyl aniline, N-methyl toluidine, N-phenyl toluidine and N-phenyl xylidine; imides such as succinimides; lactams such as ε-caprolactam and γ-valerolactam; oximes such as butanone oxime and cyclohexanone oxime; mercaptans such as methyl mercaptan, ethyl mercaptan, butyl mercaptan, 2-mercaptobenzothiazole, α-naphthyl mercaptan and dodecyl mercaptan.

To prepare the lacquer binders, the polyisocyanate (which may be blocked), polyfunctional reactants, catalysts and optionally other commonly used additives such as pigments, dyes, fillers and levelling agents are thoroughly mixed and homogenized in a conventional mixing apparatus, e.g., in a sand mill, with or without solvent or diluent.

The paints and films may be applied solvent-free or in solution or from the melt or they may be applied in solid form by the usual methods such as brush coating, roller coating, casting or spraying or the whirl-sintering process or the electrostatic powder spray process.

Lacquers containing the polyisocyanates to be used according to the invention give rise to films which have surprisingly firm adherence to metallic surfaces and are exceptionally light-fast, resistant to discoloration in the heat and abrasion-resistant and, when used in air-drying lacquers, the surface hardens exceptionally rapidly even at temperatures around 0° C. They are also distinguished by their hardness, elasticity, chemical resistance, high gloss, excellent weather resistance and high pigment absorption.

The following examples serve to explain the invention. All percentages given indicate percentages by weight.

EXAMPLE 1

This Example explains the preparation of a polyisocyanate according to the invention based on hexamethylene diisocyanate and 3-aminomethyl-3,5,5-trimethyl-cyclohexanol by dropwise addition of the amino alcohol (Method A).

2523 g (15 mol) of hexamethylene diisocyanate are heated to 130° C. under a nitrogen atmosphere. 171 g (1 mol) of 3-aminomethyl-3,5,5-trimethyl-cyclohexanol are added dropwise over a period of 1 hour. The temperature of the exothermic reaction can be controlled within a range of 130° to 140° C. by adjusting the rate of addition of the cyclohexanol. The reaction proceeds homogeneously without precipitation of urea. Stirring is continued for 10 minutes at 130° C. after all the cyclohexanol has been added. Excess hexamethylene diisocyanate is then removed by thin layer distillation under a high vacuum of 0.1 Torr at 170° C.

Yield: 749 g
Viscosity: 4500 cp (25° C.)
Isocyanate content: 21.7%

EXAMPLE 2

Liquid amino alcohols or, preferably, solid amino alcohols, in this case 6-amino-1-hexanol, may be reacted with the corresponding diisocyanate by method (B) described here.

59 g (0.5 mol) of 6-amino-1-hexanol are introduced into 1682 g (10 mol) of hexamethylene diisocyanate at room temperature. The mixture is heated to 160° C. under nitrogen. At this temperature, the crystalline solid goes into solution within one hour. The clear reaction solution then obtained is stirred for a further 5 minutes and cooled. Excess hexamethylene diisocyanate is removed by thin layer distillation under a high vacuum of 0.1 Torr/170° C.

Yield: 810 g
Viscosity: 2400 cp (25° C.)
Isocyanate content: 22.2%

EXAMPLE 3

This Example illustrates the effect of the isocyanate/amino alcohol ratio on the viscosity of the biuret-urethane polyisocyanate. Hexamethylene diisocyanate was reacted with 3-aminomethyl-3,5,5-trimethyl-cyclohexanol by Method (A) (Example 1). The results are shown in Table 1 below.

Table 1

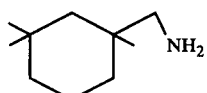

| Hexamethylene diisocyanate | OH | Viscosity (at 25° C) |
|---|---|---|
| 1009 g (6 mol) | 171 g (1 mol) | 55 000 cp |
| 1346 g (8 mol) | 171 g (1 mol) | 26 000 cp |
| 1682 g (10 mol) | 171 g (1 mol) | 13 000 cp |
| 2018 g (12 mol) | 171 g (1 mol) | 8 700 cp |
| 2523 g (15 mol) | 171 g (1 mol) | 4 500 cp |
| 3364 g (20 mol) | 171 g (1 mol) | (See Example 1) 3 800 cp |

EXAMPLE 4 (comparison experiment)

The influence of the structure of the amino alcohols is investigated with the aid of the following methods of preparation I-IV. Ethanolamine and 1-aminopropanol-3 are compared with isopropanolamine and 2-amino-2-methylpropanol-1. The first two compounds mentioned lead to unusable decomposition products while the last two compounds can be converted into low viscosity, light-colored biuret polyisocyanates.

I,1: 1680 g (10 mol) of hexamethylene diisocyanate are introduced into a stirrer vessel under an atmosphere of nitrogen, and 61 g of ethanolamine are added with stirring (see Example 2, Method B).

The mixture is heated of 140° C. with stirring. An uncontrollable exothermic reaction sets in after two hours. Although the reaction mixture still contains a high proportion of solids in the diisocyanate, the reaction is accompanied by evolution of gas. The temperature rises to 200° C. in spite of attempts to cool the reaction mixture. The product solidifies to an insoluble high polymer material.

I,2: 1682 g (10 mol) of hexamethylene diisocyanate are introduced into a three-necked flask and heated to 130° C. under nitrogen as in Method A. When this temperature has been reached, 30 g (0.5 mol) of ethanolamine are slowly added from a dropping funnel.

A precipitate immediately forms, which dissolves only slowly when a temperature of 170° C. is reached. Dropwise addition of ethanolamine is then continued at this temperature. The exothermic reaction is controlled by the rate of addition of ethanolamine and the rate of heating. After a period of three hours, by which time all the amino alcohol has been added, a sharp increase in viscosity is observed. The temperature must now be regulated by continuous cooling in an ice bath. After one more hour, the viscosity is so high that stirring cannot be continued and the experiment is stopped.

II: 1682 g (10 mol) of hexamethylene diisocyanate are heated to 180° C. under nitrogen. 38 g (0.5 mol) of 3-amino-1-propanol are added at this temperature.

A fine precipitate forms during the addition of 3-amino-1-propanol.

This precipitate gradually goes into solution as the temperature of the exothermic reaction rises to 185° C. A dark-brown end product is obtained after the addition of 3-amino-1-propanol. This end product is freed from excess hexamethylene diisocyanate by distillation in a high vacuum. The black-brown viscous product finally obtained cannot be used for light-fast lacquers.

III: 2523 g (15 mol) of hexamethylene diisocyanate are heated to 150° C. under an atmosphere of nitrogen. 75 g (1 mol) of isopropanolamine are added dropwise at this temperature over a period of one hour.

The temperature is kept within the range of 150°-155° C. by adjusting the rate of addition of isopropanolamine and the heating. The reaction proceeds without formation of a precipitate. Stirring is continued for 5 minutes after the addition of isopropanolamine. The polyisocyanate is isolated from the reaction solution by thin layer distillation.
Yield: 736 g of pale yellow liquid
Viscosity: 5000 cp (25° C.)
Isocyanate content: 20.7%

When the experiment was repeated using the same reaction mixture but
(a) increasing the time of addition of isopropanolamine (1½ hours),
(b) increasing the time of stirring after the addition of isopropanolamine (30 minutes), and
(c) increasing the reaction temperature (155°-160° C.), light-colored polyisocyanate products were again obtained, but they had higher viscosity.

IV: 2018 g (12 mol) of hexamethylene diisocyanate are introduced into a three-necked flask under an atmosphere of nitrogen and heated to 150° C. 89 g (1 mol) of 2-amino-2-methylpropanol are added dropwise from a dropping funnel over a period of 20 minutes.

The reaction mixture remains completely clear during the addition of the amino alcohol. When addition of the amino alcohol is completed, the reaction mixture is stirred for a further five minutes and cooled and the polyisocyanate is isolated by thin layer distillation at 170° C./0.1 Torr.
Yield: 684 g
Viscosity: 820 cp (25° C.)
Isocyanate content: 21.9%

When the experiment is repeated at 140° C., 160° C. and 170° C., low viscosity, light-colored polyisocyanates were again obtained even if the reaction time and the time of stirring after addition of the amino alcohols were increased.

EXAMPLES 5-35

Examples 5 to 35 are summarized in Tables 2 and 3 below. The starting materials and their quantities are summarized in Table 2 and the method, reaction temperature, yield, concentration, isocyanate content and viscosity are summarized in Table 3.

Table 2

| Ex. | Amino alcohol | Diisocyanate |
|---|---|---|
| 5 | $CH_3-CH(OH)-CH_2-CH_2-NH_2$ | 45 g (0.5 mol) hexamethylene diisocyanate 1682 g (10 mol) |

Table 2-continued

| Ex. | Amino alcohol | Diisocyanate |
|---|---|---|
| 6 | H$_2$N—[cyclohexane ring with CH$_3$ substituent]—OH | 129 g (1 mol) hexamethylene diisocyanate 1682 g (10 mol) |
| 7 | H$_2$N—CH$_2$—[cyclohexane ring]—CH$_2$—OH (mixture of isomers) | 143 g (1 mol) hexamethylene diisocyanate 2018 g (12 mol) |
| 8 | H$_2$N—CH$_2$—[norbornane/bicyclic ring]—CH$_2$—OH (mixture of isomers) | 155 g (1 mol) hexamethylene diisocyanate 2018 g (12 mol) |
| 9 | H$_2$N—[cyclohexane]—CH$_2$—[cyclohexane]—OH | 106 g (0.5 mol) hexamethylene diisocyanate 1682 g (10 mol) |
| 10 | H$_2$N—(CH$_2$)$_6$—NH—CH$_2$—CH$_2$—OH | 80 g (0.5 mol) hexamethylene diisocyanate 1682 g (10 mol) |
| 11 | H$_2$N—(CH$_2$)$_6$—NH—CH$_2$—CH(CH$_3$)—OH (mixture of isomers) | 87 g (0.5 mol) hexamethylene diisocyanate 1682 g (10 mol) |
| 12 | H$_2$N—CH(CH$_3$)—CH$_2$—NH—CH$_2$—CH$_2$—OH (mixture of isomers) | 59 g (0.5 mol) hexamethylene diisocyanate 1262 g (7.5 mol) |
| 13 | [trimethylcyclohexane ring with H$_2$N and CH$_2$—NH—CH$_2$—CH$_2$—OH substituents] | 107 g (0.5 mol) hexamethylene diisocyanate 1682 g (10 mol) |
| 14 | [trimethylcyclohexane ring with H$_2$N and CH$_2$—NH—CH$_2$—CH(CH$_3$)—OH substituents] (mixtures of isomers) | 114 g (0.5 mol) hexamethylene diisocyanate 2523 g (15 mol) |
| 15 | H$_2$N—NH—CO—O—CH$_2$—CH$_2$—OH | 40 g (0.3 mol) hexamethylene diisocyanate 1682 g (10 mol) |
| 16 | H$_2$N—NH—CO—O—CH$_2$—CH(CH$_3$)OH (mixture of isomers) | 45 g (0.3 mol) hexamethylene diisocyanate 1682 g (10 mol) |
| 17 | H$_2$N—CH$_2$—CH$_2$—NH—CO—O—CH$_2$—CH$_2$—OH | 74 g (0.5 mol) hexamethylene diisocyanate 2523 g (15 mol) |
| 18 | H$_2$N—CH(CH$_3$)—CH$_2$—NH—CO—O—CH$_2$—CH$_2$—OH (mixture of isomers) | 162 g (1 mol) hexamethylene diisocyanate 2523 g (15 mol) |
| 19 | [trimethylcyclohexane ring with H$_2$N and CH$_2$—NH—CO—O—CH$_2$—CH$_2$—OH substituents] | 258 g (1 mol) hexamethylenediisocyanate 2523 g (15 mol) |
| 20 | H$_2$N—CH$_2$—CH—NH—CO—O—CH$_2$—CH(CH$_3$)—OH (mixture of isomers) | 81 g (0.5 mol) hexamethylene diisocyanate 2523 g (15 mol) |
| 21 | H$_2$N—CH(CH$_3$)—CH$_2$—NH—CO—O—CH$_2$—CH(CH$_3$)—OH (mixture of isomers) | 176 g (1 mol) hexamethylene diisocyanate 2523 g (15 mol) |
| 22 | H$_2$N—(CH$_2$)$_6$—NH—CO—O—CH$_2$—CH(CH$_3$)—OH (mixture of isomers) | 218 g (1 mol) hexamethylene diisocyanate 2018 g (12 mol) |

Table 2-continued

| Ex. | Amino alcohol | Diisocyanate |
|---|---|---|
| 23 | [cyclohexane ring with S substituent, CH₂—NH—CO—O—CH₂—CH(CH₃)—OH, and H₂N group] (mixture of isomers) | 272 g (1 mol) hexamethylene diisocyanate 2523 g (15 mol) |
| 24 | H₂N—CH(CH₃)—CH₂—NH—CO—CH₂—(CH₂)₃—CH₂—OH (mixture of isomers) | 94 g (0.5 mol) hexamethylene diisocyanate 1009 g (6 mol) |
| 25 | [cyclohexane ring with S substituent, CH₂—NH—CO—CH₂—(CH₂)₃—CH₂—OH, and H₂N group] | 142 g (0.5 mol) hexamethylene diisocyanate 1262 g (7.5 mol) |
| 26 | CH₃—CH(OH)—CH₂—NH₂ | 75 g (1 mol) isophorone diisocyanate 2220 g (10 mol) |
| 27 | H₂N—CH₂—[cyclohexane with S]—CH₂—OH (mixture of isomers) | 72 g (0.5 mol) isophorone diisocyanate 2220 g (10 mol) |
| 28 | H₂N—CH₂—[bicyclic ring with S]—CH₂—OH (mixture of isomers) | 78 g (0.5 mol) isophorone diisocyanate 2220 g (10 mol) |
| 29 | [cyclohexane ring with S substituent, CH₂—NH₂, and HO group] | 86 g (0.5 mol) isophorone diisocyanate 3330 g (15 mol) |
| 30 | CH₃—C(CH₃)(NH₂)—CH₂—OH | 89 g (1 mol) isophorone diisocyanate 2220 g (10 mol) |
| 31 | H₂N—CH(CH₃)—CH₂—NH—CO—O—CH₂—CH(CH₃)—OH (mixture of isomers) | 88 g (0.5 mol) isophorone diisocyanate 2220 g (10 mol) |
| 32 | [cyclohexane ring with S substituent, CH₂—NH—CO—O—CH₂—CH₂—OH, and H₂N group] | 129 g (0.5 mol) isophorone diisocyanate 2220 g (10 mol) |
| 33 | H₂N—CH(CH₃)—CH₂—NH—CO—CH₂—(CH₂)₃—CH₂—OH (mixture of isomers) | 94 g (0.5 mol) isophoronediisocyanate 2664 g (12 mol) |
| 34 | [cyclohexane ring with S substituent, CH₂—NH₂, and HO group] | 171 g (1 mol) tetramethylene diisocyanate 2110 g (15 mol) |
| 35 | [cyclohexane ring with S substituent, CH₂—NH₂, and HO group] | 42 g (0.25 mol) lysine diisocyanate 636 g (3 mol) methyl ester |

Table 3

| Example | Method | Reaction temperature | Yield | Concentration[x] | Isocyanate content | Viscosity (25° C) |
|---|---|---|---|---|---|---|
| 5 | A | 130° C | 317g | 100% | 21.3% | 2500 cp |
| 6 | A | 160° C | 802g | 100% | 22.8% | 4400 cp |
| 7 | A | 150° C | 621g | 100% | 20.2% | 32000 cp |
| 8 | A | 160° C | 610g | 100% | 21.1% | 10000 cp |
| 9 | B | 170° C | 360g | 100% | 21.7% | 6000 cp |
| 10 | A | 170° C | 733g | 100% | 21.8% | 5600 cp |
| 11 | B | 180° C | 680g | 100% | 20.5% | 22000 cp |
| 12 | A | 170° C | 720g | 100% | 21.2% | 10000 cp |
| 13 | A | 140° C | 728g | 100% | 20.7% | 32000 cp |
| 14 | B | 160° C | 790g | 100% | 21.0% | 16000 cp |
| 15 | B | 180° C | 425g | 100% | 19.2% | 43000 cp |
| 16 | B | 180° C | 420g | 100% | 20.6% | 22500 cp |
| 17 | A | 180° C | 622g | 100% | 20.1% | 12000 cp |
| 18 | A | 160° C | 896g | 100% | 17.6% | 35000 cp |
| 19 | A | 160° C | 850% | 100% | 19.6% | 33000 cp |
| 20 | A | 180° C | 510g | 100% | 18.4% | 13000 cp |
| 21 | A | 160° C | 947g | 100% | 17.6% | 24000 cp |
| 22 | A | 170° C | 789g | 100% | 18.9% | 18000 cp |
| 23 | A | 160° C | 932g | 100% | 19.1% | 30000 cp |
| 24 | A | 160° C | 462g | 100% | 17.6% | 18000 cp |
| 25 | A | 160° C | 430g | 100% | 18.1% | 35000 cp |
| 26 | A | 170° C | 524g | 60% | 8.7% | 19000 cp |
| 27 | A | 170° C | 420g | 60% | 8.9% | 12000 cp |
| 28 | A | 160° C | 380g | 60% | 8.4% | 9800 cp |
| 29 | A | 160° C | 410g | 70% | 9.2% | 6500 cp |
| 30 | A | 150° C | 350g | 50% | 8.1% | 15000 cp |
| 31 | A | 160° C | 420g | 65% | 9.4% | 11000 cp |
| 32 | A | 160° C | 450g | 60% | 8.2% | 13000 cp |
| 33 | A | 160° C | 380g | 60% | 8.6% | 9500 cp |
| 34 | A | 150° C | 640g | 100% | 22.0% | 8500 cp |
| 35 | A | 170° C | 230g | 100% | 18.3% | 16000 cp |

[x] Optionally as solution in xylene/ethylene glycol monoethyl ether acetate (1:1)

EXAMPLE 36 (comparison)

Test for stability in storage

The test for the stability of the monomers was carried out over a prolonged period at 50° C., using a selection of biuret-urethane polyisocyanates shown in the following Table 4. A polyisocyanate with biuret structure based on hexamethylene diisocyanate, which had been prepared according to German Offenlegungsschrift 2,261,065 (Example 1), was tested for comparison. Whereas, in the latter case, the free hexamethylene diisocyanate content was found to increase and at the same time the product was found to contain a high proportion (16–17%) of free, 3,3'-dimethyl-4,4'-diisocyanate-dicyclohexyl methane, the polyisocyanates prepared from the various amino alcohols were found to contain only a small amount of monomeric hexamethylene diisocyanato, and this amount was practically constant within the limit of error when the product was subjected to prolonged exposure to heat.

The figures of free hexamethylene diisocyanate shown in Table 3 were determined by gas chromatography.

Table 3

| Polyisocyanate according to Example | O-Value | Free hexamethylene diisocyanate | | |
|---|---|---|---|---|
| | | 4 weeks | 8 weeks | 12 weeks |
| German Offenlegungsschrift 2,261,065 | 0.8 % | 1.2 % | 1.3 % | 1.4 % |
| 1 | 0.69% | 0.67% | 0.66% | 0.71% |
| 4-III | 0.61% | 0.63% | 0.64% | — |
| 4-IV | 0.56% | 0.56% | 0.58% | 0.57% |
| 5 | 0.58% | 0.36% | 0.47% | 0.49% |
| 7 | 0.76% | 0.69% | 0.61% | 0.79% |
| 13 | 0.69% | 0.49% | 0.45% | 0.67% |
| 14 | 0.66% | 0.68% | 0.68% | — |
| 16 | 0.8 % | 0.84% | 0.81% | — |
| 17 | 0.69% | 0.65% | — | — |
| 18 | 0.65% | 0.62% | — | — |
| 19 | 0.7 % | 0.61% | — | — |
| 20 | 0.75% | 0.62% | — | — |
| 21 | 0.58% | 0.6 % | — | — |
| 23 | 0.45% | 0.47% | — | — |

Table 3-continued

| Polyisocyanate according to Example | O-Value | Free hexamethylene diisocyanate | | |
|---|---|---|---|---|
| | | 4 weeks | 8 weeks | 12 weeks |
| 23 | 0.45% | 0.47% | — | — |

EXAMPLE 37

Low solvent lacquers were prepared using the biureturethane polyisocyanates from Examples 20 and 23, and the lacquers were tested to determine their properties.

The hydroxyl component used in this case was a polyester with a hydroxyl group content of 5.5% by weight which had been prepared from α-ethyl-hexanoic acid (14.49% by weight), benzoic acid (14.49% by weight), trimethylolpropane (45.11% by weight), phthalic acid anhydride (31.36% by weight) and maleic acid anhydride (2.84% by weight) by azeotropic condensation and dissolved in ethylglycol acetate to form an 80% solution.

The solution of the hydroxyl compound is mixed with titanium dioxide (rutile) and triturated in the usual manner, e.g., on a sand mill, to improve the wetting of the inorganic pigment. The two components, the polyisocyanate and pigmented hydroxyl compound, are then mixed together. Both lacquers have a solid content of 72% by weight (polyisocyanates from Examples 20 and 23) at a spray viscosity of 25 seconds measured in a 4mm DIN-outflow cup (DIN 53211).

The lacquers are then sprayed on sheet steel and hardened under various conditions. The following Table shows the results of the tests and the composition of the lacquers.

(Figures are given in parts by weight.)

| | Polyisocyanate from | |
|---|---|---|
| | EXAMPLE 20 | EXAMPLE 23 |
| Hydroxyl component | 100 | 100 |
| Titanium dioxide | 70 | 70 |

| | Polyisocyanate from | |
|---|---|---|
| | EXAMPLE 20 | EXAMPLE 23 |
| Ethylglycol acetate | 54 | 53 |
| Polyisocyanate | 59 | 57 |
| Thickness of layer | approx. 60μ | approx. 60μ |
| Gloss according to Gardener (ASTM D 523-536) | 94 | 93 |
| Pendulum hardness (DIN 53157) | | |
| 30' 80° C | 99" | 114" |
| 30' 120° C | 188" | 199" |
| Aging 48 h 60° C | 198" | 197" |
| Grid section (DIN 53515) | 1 | 1 |
| Erichsen-cupping (DIN 53156) | 7 mm | 6 mm |
| Solvent resistance (Hardening 30' 80° C) | | |
| Toluene - 5 min | no change | no change |
| Ethyl acetate - 5 min | " | slight swelling |
| Acetone - 5 min | " | slight swelling |
| Drying at room temperature | firm to the touch after 2 hours | firm to the touch after 2 hours |

Hardening at room temperature results in coatings which have the same excellent mechanical properties.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanates containing urethane and biuret groups and having aliphatically-bound isocyanate groups and an isocyanate functionality greater than 2, comprising reacting aliphatic and/or cycloaliphatic diisocyanates in an at least 4-times molar excess with compounds of the formula $$(H_2N)_n + X \mathord{\mathop{-}\limits_{o}} R + OH)_m$$

wherein
o represents 0 or 1,
m represents 1 or 2 when $o = 0$ and represents 1 when $0 = 1$,
n represents 1 or 2 when $o = 0$ and represents 1 when $o = 1$, such that the sum of $n + m$ is always 2 or 3,
R either
(a) represents a xylylene group when $o = 0$ or
(b) when $o = 0$ it may represent an aliphatic or cycloaliphatic hydrocarbon group having a total of 3-18 carbon atoms which may be interrupted by secondary amino groups —NH—, ether groups —O—, amide groups —NH—CO— or urethane groups —NH—CO—O— in such a manner that at least two carbon atoms are arranged between NH$_2$ and OH groups, the trimethylene group being excluded, or
(c) when $o = 1$, R represents an aliphatic hydrocarbon group having from 2-10 carbon atoms, at least 2 carbon atoms being arranged between X and the OH group, and
X represents a group —NH—CO—O— or —NH—CO—, the amino group —NH$_2$ being in each case linked to the nitrogen atom of these groups with formation of the structure of a hydrazine derivative at a temperature between about 90 and 200° C. and subsequently removing the excess diisocyanate.

2. The product of the process of claim 1.

3. In a process for the production of polyurethanes by the reaction of polyisocyanates with compounds containing hydrogen atoms reactive with isocyanate groups the improvement comprising employing the product of claim 2 as the reactive polyisocyanate.

4. The process of claim 1 wherein the compound reacted with the diisocyanate is an amino alcohol of the formula $$(H_2N)_{\overline{n}} \; R' + OH)_m$$

wherein
n and m have the same meaning as in claim 1 and
R' represents a xylylene group or an aliphatic or cycloaliphatic hydrocarbon group having a total of 13 to 18 carbon atoms with the limitation that the trimethylene group is excluded and the NH$_2$ and OH groups are separated by at least 2 carbon atoms, which hydrocarbon group may be interrupted by amino groups —NH—, ether groups —O—, amido groups —NH—CO— or urethane groups —NH—CO—O—.

5. The process of claim 4 wherein R' represents an aliphatic hydrocarbon group with a total of 4 to 10 carbon atoms which may be interrupted by a urethane group —NH—CO—O— or a cycloaliphatic or mixed cycloaliphatic-aliphatic hydrocarbon group with a total of 6 to 15 carbon atoms which may be interrupted by a urethane group —NH—CO—O.

6. The process of claim 1 wherein the compound reacted with the diisocyanate is a hydrazine derivative with a hydroxyl group as represented by the formula

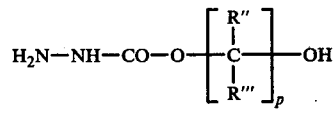

in which
R" and R''' represent the same or different groups and represent hydrogen or a C$_1$-C$_4$-alkyl group,
p represents 2 or 3.

7. The process of claim 6 wherein R" and R''' represent hydrogen or a methyl group.

8. The process of claim 1 wherein the compound reacted with the diisocyanate is a hydrazine derivative of the formula

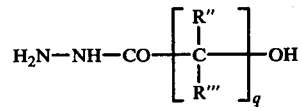

in which
R" and R''' have the meaning indicated in claim 6, and
q represents an integer of from 4 to 10.

9. The process of claim 8 wherein q represents 5.

10. The process of claim 1 wherein
(a) a 6 to 25 molar excess of isocyanate is used,
(b) the reaction is conducted at about 120 to 180° C., and
(c) the reaction is solvent free.

11. The process of claim 10 wherein
(a) the diisocyanate is hexamethylene diisocyanate or isophorone diisocyanate, and
(b) the excess diisocyanate is removed by thin film evaporation.

12. A process for the production of a two-component polyurethane lacquer binder comprising combining compounds containing reactive groups selected from the group consisting of —OH, —SH, —NH, and —COOH with the polyisocyanate of claim 2 in an active group to NCO group ratio of between about 0.8:1 and 3:1.

13. The lacquer binder produced by the process of claim 12.

14. A process for the production of moisture curing polyurethane lacquers comprising reacting compounds containing hydroxyl groups with the polyisocyanate of claim 2 at an NCO to OH ratio of between about 1.2:1 and 10:1.

15. The lacquer produced by the process of claim 14.

16. A process for coating comprising applying to a substrate a polyurethane lacquer comprising the polyisocyanate of claim 2 and a polyhydroxyl compound.

* * * * *